United States Patent [19]

Artiss et al.

[11] Patent Number: 5,310,679

[45] Date of Patent: * May 10, 1994

[54] COMPOSITION FOR REDUCING TURBIDITY IN SAMPLES OF BIOLOGICAL FLUIDS

[76] Inventors: Joseph D. Artiss, 2761 Avondale Court, Windsor, Ontario, Canada, N9E 1X1; Bennie Zak, 6692 Maple Lakes Dr., West Bloomfield, Mich. 48033

[*] Notice: The portion of the term of this patent subsequent to Dec. 2, 2003 has been disclaimed.

[21] Appl. No.: 936,267

[22] Filed: Dec. 1, 1986

Related U.S. Application Data

[63] Continuation-in-part of Ser. No. 733,267, May 13, 1985, Pat. No. 4,626,511.

[51] Int. Cl.$^5$ .............................................. G01N 31/00
[52] U.S. Cl. ........................................ 436/18; 436/8; 436/17; 436/13; 436/176; 252/408.1
[58] Field of Search .................. 435/4, 11, 17, 18, 19, 435/25, 28, 188; 436/8–19, 176; 252/408.1; 424/3, 11, 7.1

[56] References Cited

U.S. PATENT DOCUMENTS

| | | | |
|---|---|---|---|
| 3,168,448 | 2/1965 | Melcer et al. | 195/66 |
| 3,260,648 | 7/1966 | Fox | 167/84 |
| 3,703,591 | 11/1972 | Bucolo et al. | 195/103 R |
| 3,759,793 | 9/1973 | Stork et al. | 195/103 R |
| 3,853,465 | 12/1974 | Rush et al. | 23/230 B |
| 3,955,925 | 5/1976 | Proksch et al. | 436/13 |
| 4,011,045 | 3/1977 | Bonderman | 23/230 B |
| 4,012,287 | 3/1977 | Carl et al. | 195/103 R |
| 4,066,508 | 1/1978 | Rauscher et al. | 195/99 |
| 4,216,117 | 9/1980 | Proksch et al. | 436/13 |
| 4,226,713 | 10/1980 | Goldberg | 436/13 |
| 4,245,041 | 1/1981 | Denney | 435/15 |
| 4,264,471 | 4/1981 | Briggs | 436/18 |
| 4,309,502 | 1/1982 | Lauderdale | 435/15 |
| 4,338,395 | 7/1982 | Leon et al. | 435/17 |
| 4,370,311 | 1/1983 | Ilekis | 436/13 |
| 4,465,774 | 8/1984 | Huang et al. | 436/13 |
| 4,486,531 | 12/1984 | Ziegenhorn et al. | 436/13 |
| 4,489,162 | 12/1984 | Hawkins et al. | 436/15 |
| 4,503,146 | 3/1985 | Yun et al. | 436/13 |
| 4,626,511 | 12/1986 | Artiss et al. | 436/18 |

*Primary Examiner*—Robert A. Wax
*Assistant Examiner*—T. J. Wallen
*Attorney, Agent, or Firm*—Weintraub, DuRoss & Brady

[57] ABSTRACT

A composition which reduces the turbidity of samples of artificial or naturally occurring biological fluids comprising:
 a buffering agent;
 a nonionic surfactant;
 a lipolytic enzyme; and water.

The composition provides a catalyst for and agents which hydrolyze triglycerides present in the sample to glycerol and free fatty acids. Also present in the composition is a fatty acid scavenging agent or agents to render the catalyzed fatty acids water-soluble. The fatty acid scavenging agent may be cyclodextrin, albumin or mixtures thereof.

21 Claims, 2 Drawing Sheets

COMPOSITION FOR REDUCING TURBIDITY IN SAMPLES OF BIOLOGICAL FLUIDS

RELATED APPLICATION

This application is a continuation-in-part of U.S. patent application Ser. No. 733,267, filed May 13, 1985 now U.S. Pat. No. 4,626,511.

BACKGROUND IN THE INVENTION

1. Field of the Invention

The present invention relates to a means and method of analyzing naturally occurring and artificially produced biological fluids. More particularly, the present invention concerns a means and method of reducing turbidity in various biological samples for other biological assays, for example hemoglobin determination, whole blood, glucose, neonatal bilirubin, cholesterol and/or triglycerides in blood serum or plasma.

2. Prior Art

Many assays of biological fluids such as glucose, albumin, etc., in whole blood or plasma, require colorimetric methods of analysis. In such samples, elevated triglyceride levels interfere with accurate determinations by causing sample turbidity which poses prblems during analysis.

Blood assays to determine total blood hemoglobin are a necessary element of medical blood work-ups. To ascertain hemoglobin content of blood, hemoglobin is conventionally converted to cyanomethemoglobin using Drabkin's reagent. However, the presence of elevated levels of triglycerides in both whole blood and plasma samples causes turbidity during conventional analysis. The turbidity created by the triglycerides in the samples creates difficulties in determining the hemoglobin content of the sample. Turbidity has deleterious effects on measurements requiring optical analysis and in radioimmunoassays.

To overcome problems of turbidity many means and methods have been developed. Presently, the predominant approaches are ultracentrifugation, organic solvent extraction or chemical precipitation of the lipoproteins. These are time-consuming, arduous and cumbersome techniques.

Exemplifying the prior art is, for example, U.S. Pat. No. 4,309,502. This patent teaches a reagent kit for the hydrolysis of triglycerides to glycerol a nd free fatty acids using lipase, and at least one reagent capable of assaying glycerol. The invention disclosed in this reference is predicated on the use of a microbial source of lipase such as *Chromobacterium viscosum*, which, in turn, requires activation by the presence of a surfactant.

Other relevant art is found in U.S. Pat. Nos. 4,338,395; 3,168,448; 3,759,793; 4,245,041; 3,703,591; 4,012,287 and 3,853,465.

In McGowan et al, *Clinical Chemistry*, vol. 29, No. 3, 1983, there is described a totally enzymatic technique for measuring triglycerides involving the complexation of generated fatty acids thus eliminating the production of turbidity.

None of the prior art is directd to the elimination of triglycerides to reduce the rurbidity generated thereby. It is to be appreciated that the prior art fails to provide a simple, one-step reagent which overcomes the turbidity in samples of biological fluids to permit sample assaying. It is to this purpose that the present invention is directed.

SUMMARY OF THE INVENTION

In accordance with the present invention there is provided a reagent composition for reducing turbidity in samples of artificial or naturally occurring biological fluids comprising:
 a) a buffering agent;
 b) a nonionic surfactant;
 c) a lipolytic enzyme; and
 d) water.

The reagent of the present invention may also contain a fatty acid scavenging agent to assist in the complexing of fatty acids formed by the hydrolysis of triglycerides present in the sample.

The reagent of the present invention, when added to whole blood, serum or p;asma, reduces turbidity and permits accurate measurement of, for example, hemoglobin, glucose and total protein in lipemic whole blood, serum and plasma samples. Likewise, the present composition can be used to reduce turbidity caused by triglycerides in other naturally occurring or artificial bilogical fluids.

In use, the reagent composition can be added directly to the sample to be analyzed to clarify the sample. The reagent composition can be admixed with conventional colorimetric indicators such as Drabkin's reagent and the modified reagent added to the sample to be analyzed. The reagent composition hereof can be applied to automated instrumentation without deleterious affects.

For more complete understanding of the present invention, reference is made to the following detailed description and accompanying examples.

DESCRIPTION OF THE PREFERRED EMBODIMENTS

In accordance with the present invention there is provided a reagent for reducing turbidity in biological fluids and, in particular, in lipemic whole blood, serum or plasma or other biological fluids, to permit hemoglobin, albumin, glucose and total protein analysis. The reagent of the present invention comprises:
 a) a buffering agent;
 b) a nonionic surfactant;
 c) a lipolytic enzyme;
 d) a fatty acid scavenging agent; and
 e) water.

It is to be appreciated by those skilled in the art to which the present invention pertains that the reagent of the present invention can be admixed with various conventional analytical reagents such as Drabkin's reagent and the like. Drabkin's reagent is a well-known reagent for assaying hemoglobin which is an admixture of potassium ferricyanide and an alkali metal cyanide, preferably, either potassium or sodium cyanide.

The buffering agent employed in the present invention can be any well-known buffering agent which adequately maintains the pH of the reaction mixture, i.e., having a pH in the range of about 3.0 to about 10.0. Representative of the buffering agents which can be used herein include sodium carbonate, sodium bicarbonate, sodium hydroxide, potassium phosphate, sodium phosphate and the like, as well as mixtures thereof. The buffering agent selected will vary depending upon the analyte and type of biological fluid solution to be analyzed.

As is reported in U.S. Pat. No. 4,011,045, the addition of a nonionic surfactant aids in the dissolution of triglycerides. Nonionic surfactants serve to activate or catalyze the lipolytic enzyme which promotes the decomposition of triglycerides to glycerol and free fatty acids. Preferably, a nonionic surfactant, such as an ethylene oxide adduct of an alkyl phenol is employed. These surfactants are well known and commercially available, such as the ethylene oxide adduct of a nonylphenol sold by Rohm & Hass under the name Triton X-100. Likewise, ethylene oxide adducts of an octyl phenol can be employed herein.

A lipolytic enzyme is used in admixture with the other components of the reagent hereof. The lipolytic enzyme is selected from the group consisting of lipase, esterase and mixtures thereof. The lipase and esterase are, or course, enzymes of microbial origin which hydrolyze triglycerides. Preferably, the lipase employed herein is of *Chromobacterium viscosum*. Where high levels of cholesterol are encountered, a lipase-esterase blend can be advantageously employed. In such instances, the lipase is of *Chromobacterium viscosum* and the esterase is also of microbial origin and is commercially available from Finnsugar Bicohemical Corporation.

The utilization of the lipolytic enzyme involves the efficient and rapid catalysis of the hydrolysis of the triglycerides to glycerol and free fatty acids. The advantage of lipase or a lipase-esterase blend is that this enzyme provides for clarification of the srum over a broad pH range from about 3 to about 10 in a period less than or equal to five minutes; the time required for most colorimetric reactions.

The reagent composition of the present invention may also contain a fatty acid scavenging or complexing agent to render the lipolytically generated fatty acids water soluble. This enables clarification of the sample directly without the need for separation of the lipids from the sample. The fatty acid scavenger is preferably selected from the group consisting of cyclodextrin, albumin and mixtures thereof. Both cyclodextrin and albumin are commercially availabe products and are well known. The cyclodextrin employed in this invention can be either alpa- beta- or gamma cyclodextrin or mixtures thereof. The albumin employed may be of any type commercially available. It is to be understood that the albumin empolyed need not be of bovine origin.

It is to be understood that, in samples to be analyzed for albumin content, cyclodextrin is advantageously employed. In certain instances, albumin may be successfully substituted as a fatty acid scavenger. One such analytical procedure is the analysis or assay for neonatal bilirubin in which the amount of bilirubin present is measured as a bilirubin-albumin complex.

It is also to be understood that, in certain instances, the fatty acid scavenger can be omitted entirely. This may be successfully accomplished when the fatty acid concentration is particularly low.

In preparing the reagent composition of the present invention, generally, from about 100 to 6000 kilo units (KU) of the lipase per liter of the buffered aqueous solution is employed. Preferably, from about 200 to 4500 KU of lipase is employed.

Where a lipase-esterase blend is employed, the amount of esterase employed is between about 100 and about 450 U microliters (μl). As in reagents containing solely lipase, from about 100 to about 6000 KU of lipase blend per liter of buffered aqueous solution is employed. Preferably, from about 200 to about 4500 KU of the enzyme blend is employed.

The introduction of a lipase-esterase blend is particularly useful in samples containing high levels of cholesterol. In such samples, the rate of hydrolysis was unexpectedly increased by the presence of a lipase-esterase blend over that triggered by either lipase or esterase independently.

Cyclodextrin is employed in an amount ranging up to about 10.0 grams per liter of buffered aqueous solution and is preferably present in an amount ranging from about 3.0 grams to about 8.0 grams thereof per liter of reagent.

When albumin is employed in an amount ranging from about 10.0 grams/L to about 30.0 grams/L and is preferably present in an amount ranging between about 15.0 grams to about 25.0 grams thereof per liter of reagent. The surfactant is employed in an amount ranging from about 0.1 to about 1.0 grams thereof per liter of buffered aqueous solution and is, preferably, present in an amount ranging from about 0.25 to about 0.75 grams thereof per liter of the buffered aqueous solution.

The buffering agent is employed in an amount sufficient to yield a solution pH optimal for the analysis to be performed.

In preparing the reagent composition hereof the components are admixed together under ambient conditions.

In practice, the addition of the composition of the present invention to samples, blood, plasma, serum or other biological fluids, directly results in the reduction of turbidity of the sample by the direct hydrolysis of the triglycerides to glycerol and free fatty acids and the subsequent complexation of the fatty acids by the cyclodextrin.

When analyzing whole blood hemoglobin, the composition of the present invention is admixed with conventional Drabkin's reagent. When a blood sample is added, the clearing of the triglycerides occurs within the known period for the reaction of hemoglobin with potassium ferricyanide and potassium cyanide to yield a cyanmethemoglobin and the mixture does not interfere with that reaction.

For a more complete understanding of the present invention reference is made to the following examples. The examples are intended to be illustrative and not limitative of the present invention.

ANALYTICAL PROCEDURE

In the following examples of the present invention, the reagent hereof is employed in an additive to a conventional colorimetric reagent, i.e., Drabkin's reagent. In carrying out the examples, a stock solution based upon one liter of Drabkin's reagent was employed. To one liter of Drabkin's reagent was added the reagent hereof which has the following composition:
 3,400 KU of lipase;
 4.0 grams of alpha-cyclodextrin;
 0.5 grams Triton X-100.

This mixture is stable for at least six weeks when stored refrigerated in a dark bottle.

In practicing the present invention, the blood and serum samples used were freshly discarded samples obtained from a hematology laboratory.

Grossly lipemic whole blood was prepared by resuspending saline-washed red cells in either an intravenous fat emulsion or a triglyceride-rich serum having triglyceride concentrations of about 70 grams per liter. Chylomicrons were harvested by separating them from severely lipemic serums in which the refrigeration test showed marked elevations.

The determination of hemoglobin in the lipemic blood was carried out by adding five microliters (5µl) of a blood sample to one and a half milliliters (1.5 ml) of the modified Drabkin's reagent. The solution was then thoroughly mixed and incubated at 37° C. for a minimum of five minutes.

The absorbance of the sample was measured at 540 nanometers (nm) using a Model 25 Beckman spectrophotometer equipped with a flow-through, thermostated microcuvet. The absorbances of the samples and standard at 540 nm were measured versus a reagent blank in which deionized water was substituted for the sample.

EXAMPLE I

Figure 1:
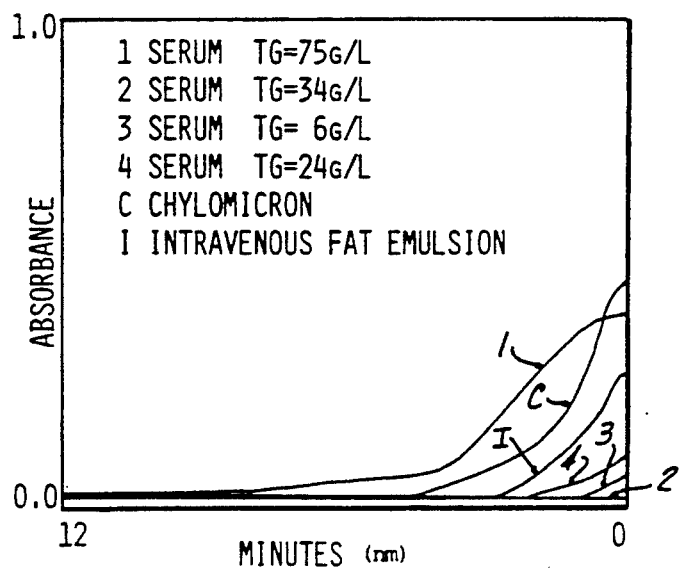
FIG. 1 graphs the decrease in absorbance of cyamethemoglobin.

In order to study the clarification potential of the Drabkin's reagent modified by the present invention, the catalytic activity of the formulation of Example I on different turbid substrates was determined by measuring the decrease in absorbance at the cyanmethemoglobin peak of 540 nm. The results are graphed in FIG. 1. The substrates of clinical interest were chylomicrons (C), intravenous fat emulsion (i) and several serums containing triglycerides at concentrations of 6 g/L, 24 g/L, 34 g/L and 75 g/L respectively. The samples having low level triglyceride contents were clarified very quickly. All assays showed transparent characteristics on spectral inspection after five minutes. Clarification of all lipemic serum samples occurred within five minutes of treatment. Thus, under these conditions, clarification of the sample specimens occurs within the time limit required for the conversion of hemoglobin to cyanmethemoglobin, which also takes approximately five minutes for completion.

EXAMPLE II

Figure 2:
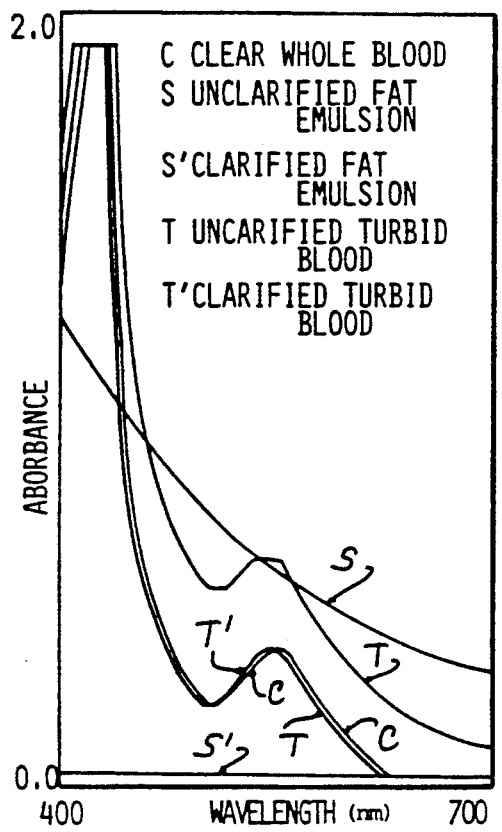
FIG. 2 shows the spectra abtained from serum according to the invention.

To demonstrate that the components of the modified Drabkin's reagent of the present inventioon do not interfere in the formation of cyanmethemoglobin, the modified Drabkin's reagent was applied to two clear, whole blood samples. In the samples, the plasma was totally replaced with either a solution of total parenteral nutrition or a severely lipemic serum. The typical spectra obtained are shown in FIG. 2. The post clarification spectrum (T') is that of the original clear sample (C) indicating the absence of any interference with cyanmethemoglobin formation.

EXAMPLE III

Figure 3:
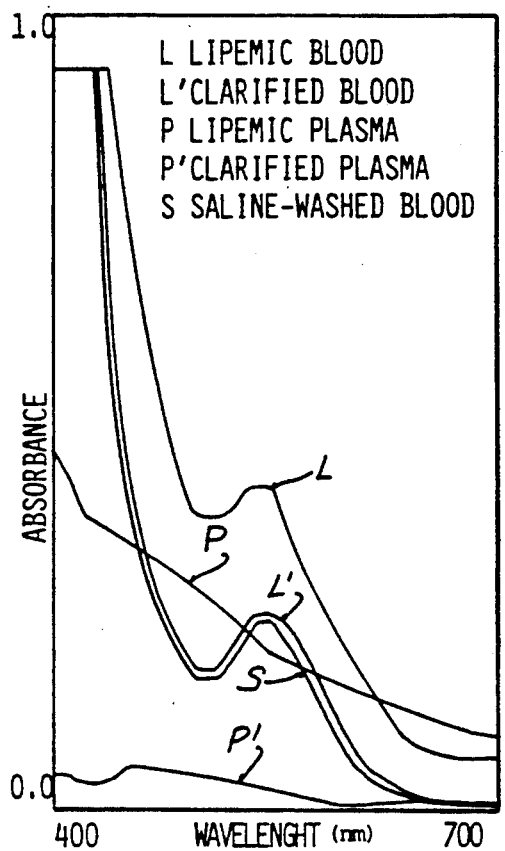
FIG. 3 shows the plazma spectra before and after enzyme clarification.

A severely lipemic whole blood specimen was treated with the modified Drabkin's reagent of the present invention. The results are set forth in FIG. 3. The lines designated P and P' are the spectra of the plasma before and after enzymic clarification and alphacyclodextrin fatty acid scavenging. In like manner, spectrum L is the original specimen treated with unmodified Drabkin's reagent where L' is the clarified specimen and S is saline-washed whole blood.

EXAMPLE IV

The applicability of the present invention to determine hemoglobin was next studied using:
(i) a hemoglobin solution having a hemoglobin concentration of 140 grams per liter prepared from washed erythrocytes and diluted with sera of different turbidities thus simulating lipemic whole blood; and
(ii) whole blood from hyperlipidemic patients.

The results are shown in Table I.

As set forth in Table I, the turbidity resulting from elevated triglyceride concentrations can cause significant increase in the hemoglobin values. The sample diluted with chylomicrons showed the largest increase in absorbance, suggesting that hemoglobin values are significantly elevated in hyperlipidemic specimens.

The results of hemoglobins assays in lipemic patient specimens is shown in Table II. The post-clarification hemoglobin value corresponds closely to the recommended procedure of re-suspending the red cells in clear serum or physiological saline; methods previously described and recommended in the literature.

EXAMPLE V

The effect of the presence of triglycerides in samples for bilirubin analysis was determined by a series of spectrophotometric tests using a Beckman Model 25 Spectrophotometer. In the analysis performed, bilirubin is measured as a bilirubin/albumin complex.

Figure 4:
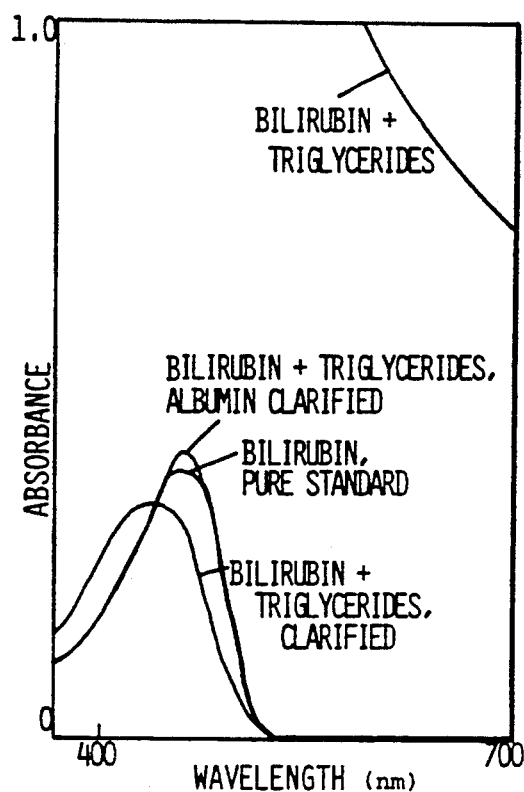
FIG. 4 shows the spectra of a bilirubin sample.

A bilirubin standard containing 243 mmol/L bilirubin was analyzed. The spectrum is set forth in FIG. 4. A bilirubin standard solution having the same concentration was spiked with Intralipid at a concentration of 12 g/L. The spectrum is shown in FIG. 4. This spectrum is grossly distorted and mostly off-scale illustrating the difficulties inherent in obtaining accurate bilirubin analysis of grossly lipemic samples.

A 30 µL sample of the Intralipid-spiked bilirubin standard was cleared using 1 milliliter of an enzyme clearing reagent prepared according to the present invention containing 4000 KU lipase, 4.0 g α-cyclodextrin and 5.0 millimoles $Na_2HPO_4$ per liter of water. The enzyme clearing reagent was admixed with the standard and allowed to incubate for 3 minutes. Clarification of this simulated lipemic sample by the enzymic-cyclodextrin reagent yielded a spectrum labeled "Bilirubin+Triglycerides, clarified" in FIG. 4. A hypochromic shift in the spectral peak from 465 nm to 445 nm occurred in the spectral analysis of this sample together with a slightly depressed peak absorbance.

Without being bound to any theory, it is believed that this aberration is due to the displacement of bilirubin from its binding sites on albumin by the large amounts of free fatty acids released during hydrolysis of the triglyceride by lipase.

A second enzyme clearing reagent was made in which the αcyclodextrin was increased. However, addition of more cyclodextrin to bind the interfering fatty acids lead to the formation of the fatty acid cyclodextrin complex.

A third enzyme clearing reagent was made containing 4000 KU lipase, 4.0 g of αcyclodextrin and 20 g of bovine serum albumin in one liter of 5.0 mmol/L $Na_2HPO_4$ buffered water. One milliliter of the third enzyme clearing reagent was admixed with a 30 μl, a sample containing the Intralipid-spiked bilirubin standard. The sample was incubated for three minutes and analyzed. The spectral curve is set forth in FIG. 4. The spectral curve closely paralleled that of the pure bilirubin standard.

EXAMPLE VI

Using a reagent containing 4000 KU lipase, 4.0 g of α-cyclodextrin and 20 g of bovine serum albumin in one liter of 5.0 mmol/L $Na_2HPO_4$ buffered solution, clarification of samples containing Intralipid (at levels as high as 16 g/L triglyceride as Intralipid) levels commonly achieved during infusions was rapid (usually less than 2 minutes) at an absorbance of 454 nm at room temperature. The added albumin appears to prevent the initially-found spectral shift of the bilirubin-albumin reagent of the present invention prevents distortion of the spectral and permits more accurate measurement.

EXAMPLE VII

Figure 5:
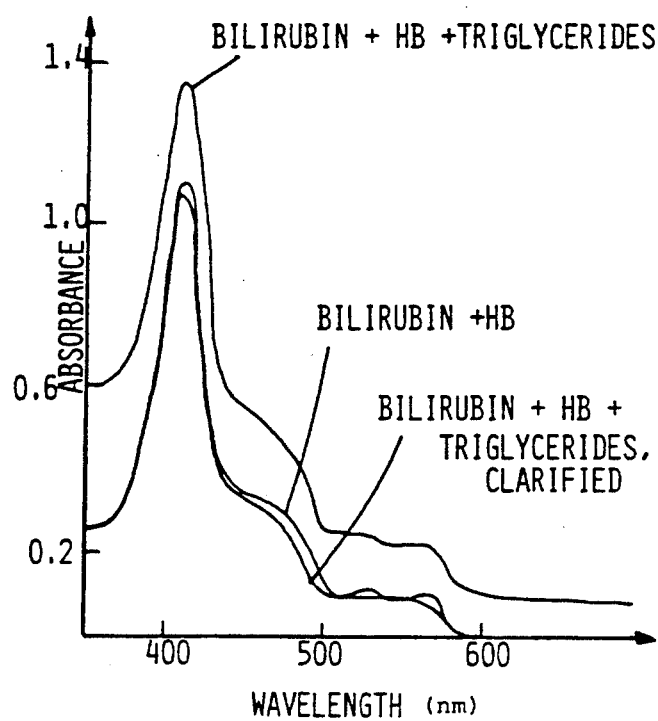
FIG. 5 shows the absorbance of a clarified and turbid sample.

In order to determine the accuracy of the enzyme clarification system when used with hemolysed lipemic bilirubin samples, a sample containing a bilirubin standard having a concentration of 173 μmol/L was spiked with Intralipid and hemoglobin to yield a triglyceride concentration of 1.2 g/L and a hemoglobin concentration of 4.9 g/L. The spectrum of the turbid sample was determined and is reproduced in FIG. 5. The mid-visible range peaks are distorted as shown in the spectral tracing labeled "Bilirubin+Hb+Triglycerides" in the turbid sample.

A 30 μL portion of this spiked sample was clarified using 1 ml of the reagent described in Example VI. The absorbance spectra of the clarified sample was determined and is reproduced in FIG. 5.

A spectral tracing of pure hemolysed bilirubin was also obtained and compared to the first two samples. The spectra of the clarified lipemic sample was within experimental error. The 173 μmol/L bilirubin standard contaminated with hemoglobin and triglyceride yielded 171 and 193 μmol/L bilirubin with and without clarification, respectively, when measured biochromatically according to a Bilirubin Stat Analyzer Photometer, Model BRII available from Advanced Instruments, Needham Heights, Mass. at wavelengths of 454 nm and 540 nm.

EXAMPLE VIII

The effect of total parenteral nutrition in samples assayed for bilirubin by the Bilirubin-Stat Analyzer is indicated in Table III using Intralipid-spiked neonatal serums. It can be observed that the enzymic-clearing reagent of the present invention as set forth in Table III has no detrimental effect on total and direct bilirubin assays in clear specimens (0 g/L Intralipid). Spurious bilirubin measurements begin in untreated samples containing greater than 2 g/L of Intralipid. Pretreatment of the sample with the enzymic-clearing reagent avoids over estimation of the total bilirubin values.

Direct bilirubin levels are also affected by the presence of lipemia as shown in Table III. However, as seen in this table, pre-treatment of samples with the enzymic-clearing reagent of the present invention eliminated these erroneous results.

Thus, it can be seen from these examples that the modified Drabkin's reagent and method of employing it reduce sample turbidity and determine hemoglobin content of blood samples provides an accurate and efficient method of blood analysis.

TABLE I

Cleared and uncleared hemoglobin values for samples prepared by diluting a hemoglobin solution (140 g/L) 1:1 with various sera.

| Media | Absorbance* | | Hemoglobin (g/L)* | |
|---|---|---|---|---|
| | Uncleared | Cleared | Uncleared | Cleared |
| Chylomicrons | 0.634 | 0.156 | 280 | 69 |
| Turbid serum (triglycerides = 33.6 g/L) | 0.202 | 0.161 | 89 | 71 |
| Turbid serum (triglyceride = 12.5 g/L) | 0.239 | 0.162 | 105 | 71 |
| Turbid serum (triglyceride = 5.74 g/L) | 0.170 | 0.160 | 75 | 71 |
| Clear serum | 0.162 | 0.162 | 71 | 71 |
| Clear serum | 0.162 | 0.159 | 71 | 70 |
| Clear serum | 0.161 | 0.161 | 71 | 71 |

*Average of duplicate values

TABLE II

Hemoglobin values for patient specimens (lipemic whole blood) before and after clarification and compared to the recommended procedure of plasma replacement with saline.

| | Hemoglobin Concentration (g/L)* | | |
|---|---|---|---|
| | Patient Whole Blood | | |
| No. | Uncleared | Cleared | RBC in Saline |
| 1 | 157 | 145 | 144 |
| 2 | 125 | 107 | 108 |
| 3 | 111 | 104 | 102 |
| 4 | 202 | 122 | 112 |

*Average of triplicates

TABLE III

BILIRUBIN QUANTITATION IN INTRALIPID-SPIKED NEONATAL SERA[a]

| Intralipid added (g/l) | Total bilirubin (mol/l) | | | Direct bilirubin (mol/l) | | |
|---|---|---|---|---|---|---|
| | Theoretical | Without clarification | With clarification | Theoretical | Without clarification | With clarification |
| 0 | — | 345 | 347 | — | 165 | 161 |
| 0 | — | 35 | 36 | — | 12 | 14 |
| 0 | — | 19 | 19 | — | 3 | 3 |
| 0 | — | 94 | 99 | — | 54 | 50 |
| 0 | — | 14 | 12 | — | 3 | 5 |
| 0 | — | 125 | 125 | — | 57 | 54 |
| 1.0 | 341 | 336 | 364 | 163 | 177 | 161 |
| 2.0 | 19 | 61 | 17 | 3 | 3 | 5 |
| 3.0 | 33 | 90 | 36 | 12 | 0 | 14 |
| 3.9 | 90 | 153 | 101 | 52 | 31 | 47 |
| 4.8 | 14 | 94 | 16 | 3 | 10 | 5 |

TABLE III-continued

| | BILIRUBIN QUANTITATION IN INTRALIPID-SPIKED NEONATAL SERA[a] | | | | | |
|---|---|---|---|---|---|---|
| | Total bilirubin (mol/l) | | | Direct bilirubin (mol/l) | | |
| Intralipid added (g/l) | Theoretical | Without clarification | With clarification | Theoretical | Without clarification | With clarification |
| 9.1 | 113 | 161 | 121 | 52 | * | 54 |

[a]Results shown as mean of duplicate analyses
*Could not be measured

We claim:

1. A composition for reducing turbidity in fluid samples consisting essentially of:
   a buffering agent;
   a nonionic surfactant;
   a lipolytic enzyme; and
   water.

2. The composition of claim 1 wherein the lipolytic enzyme is selected from the group consisting of lipase, esterase, or mixtures thereof.

3. The composition of claim 2 wherein the lipase is derived from *Chromobacterium viscosum*.

4. the composition of claim 2 wherein the esterase is derived from a microbial source.

5. The composition of claim 2 wherein the lipolytic enzyme is present at a concentration in the range of about 100 to about 6000 kilounits enzyme per liter of water.

6. The composition of claim 5 wherein the lipolytic enzyme is present in the range of about 200 to about 4500 kilounit enzyme per liter of water.

7. The composition of claim 6 wherein the esterase is present in an amount between about 100 UL to about 450 UL.

8. The composition of claim 2 wherein the nonionic surfactant is an ethylene oxide adduct of an alkyl phenol.

9. The composition of claim 2 wherein the nonionic surfactant is an ethylene oxide adduct of a nonylphenol.

10. The composition of claim 2 wherein the nonionic surfactant is an ethylene oxide adduct of an octyl phenol.

11. The composition of claim 2 wherein the surfactant is employed in an amount ranging from about 0.1 to about 1.0 grams thereof per liter of buffered aqueous solution.

12. The composition of claim 2 wherein the surfactant is present in an amount ranging from about 0.25 to about 0.75 grams per liter of water.

13. The composition of claim 2 wherein the buffering agent is employed in an amount sufficient to yield a solution pH between about 3.0 and about 10.0.

14. A composition for reducing turbidity in fluid samples consisting essentially of:
   a buffering agent;
   a nonionic surfactant;
   a lipolitic enzyme selected from the group consisting of lipase, esterase, or mixtures thereof;
   water; and
   a fatty acid scavenging agent.

15. The composition of claim 14 wherein the fatty acid scavenger is selected from the group consisting of cyclodextrin, albumin and mixtures thereof.

16. The composition of claim 15 wherein the fatty acid scavenger is a cyclodextrin selected from the group consisting of alpha-cyclodextrin, beta-cyclodextrin, gamma-cyclodextrin or mixtures thereof.

17. The composition of claim 15 wherein the fatty acid scavenging agent is employed inan amount from about 1.0 to about 10.0 grams per liter of water.

18. The composition of claim 15 wherein albumin is employed in an amount ranging from about 10.0 to about 30.0 grams per liter of water.

19. The composition of claim 15 wherein albumin is employed in an amount ranging from about 15.0 to about 25.0 grams per liter of reagent.

20. The composition of claim 15 wherein cyclodextrin is employed in an amount ranging from about 1.0 to about 10.0 grams per liter of reagent.

21. A composition for reducing turbidity in dluid samples consisting essentially of:
   an ethylene oxide adduct of nonylphenol;
   a lipolytic enzyme selected from the group consisting of lipase, esterase, or mixtures thereof;
   a fatty acid scavengng agent selected from the group consisting of cyclodextrin, albumin or mixtures thereof; and
   water.

* * * * *